US00PP33682P2

(12) United States Plant Patent
Vlielander

(10) Patent No.: US PP33,682 P2
(45) Date of Patent: Nov. 23, 2021

(54) ***KALANCHOE* PLANT NAMED 'DOKALCASI'**

(50) Latin Name: *Kalanhchoe blossfeldiana*
Varietal Denomination: Dokalcasi

(71) Applicant: DUMMEN GROUP B.V., De Lier (NL)

(72) Inventor: Ike J. Vlielander, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/196,771

(22) Filed: Mar. 9, 2021

(51) Int. Cl.
*A01H 5/02* (2018.01)
*A01H 6/32* (2018.01)

(52) U.S. Cl.
USPC ..... Plt./335

(58) Field of Classification Search
USPC ..... Plt./335
See application file for complete search history.

*Primary Examiner* — Susan McCormick Ewoldt
(74) *Attorney, Agent, or Firm* — C. Anne Whealy

(57) ABSTRACT

A new and distinct cultivar of *Kalanchoe* plant named 'Dokalcasi', characterized by its relatively large, upright and uniformly mounded plant habit; vigorous growth habit and rapid growth rate; freely branching plant habit; dark green-colored leaves; uniform, early and freely flowering habit; large single-type deep pink and pale purplish pink bi-colored flowers; and excellent postproduction longevity and garden performance.

2 Drawing Sheets

Figure 1:
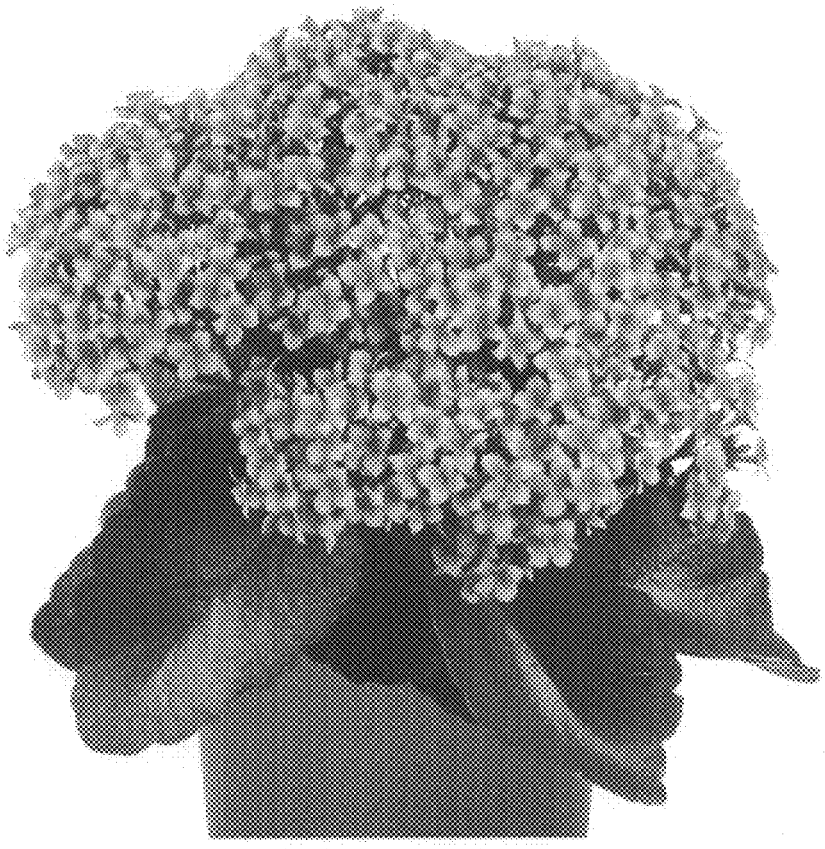

Botanical designation: *Kalanchoe blossfeldiana.*
Cultivar denomination: 'DOKALCASI'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Nov. 9, 2020, application number 2020/2814. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Kalanchoe* plant, botanically known as *Kalanchoe blossfeldiana* and hereinafter referred to by the name 'Dokalcasi'.

The new *Kalanchoe* is a product of a planned breeding program conducted by the Inventor in De Lier, The Netherlands. The objective of the breeding program is to create new relatively large-growing, freely-branching and freely-flowering *Kalanchoe* plants with attractive leaf and flower coloration that are suitable for container and garden use.

The new *Kalanchoe* plant originated from a cross-pollination made by the Inventor in De Lier, The Netherlands in October, 2012 of *Kalanchoe blossfeldiana* 'Forever Maxi Yellow', not patented, as the female, or seed, parent with

*Kalanchoe blossfeldiana* 'Taranak', not patented, as the male, or pollen, parent. The new *Kalanchoe* plant was discovered and selected by the Inventor as a single flowering plant from within the progeny of the stated cross-pollination in a controlled greenhouse environment in De Lier, The Netherlands in August, 2013.

Asexual reproduction of the new *Kalanchoe* plant by vegetative terminal cuttings in a controlled greenhouse environment in De Lier, The Netherlands since May, 2014 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalcasi'. These characteristics in combination distinguish 'Dokalcasi' as a new and distinct *Kalanchoe* plant:

1. Relatively large, upright and uniformly mounded plant habit.
2. Vigorous growth habit and rapid growth rate.
3. Freely branching plant habit.
4. Dark green-colored leaves.
5. Uniform, early and freely flowering habit.
6. Large single-type deep pink and pale purplish pink bi-colored flowers.
7. Excellent postproduction longevity and garden performance.

Plants of the new *Kalanchoe* can be compared to plants of the female parent, 'Forever Maxi Yellow'. Plants of the new *Kalanchoe* differ from plants of 'Forever Maxi Yellow', in the following characteristics:

1. Plants of the new *Kalanchoe* are larger and more vigorous than plants of 'Forever Maxi Yellow'.
2. Flowers of plants of the new *Kalanchoe* are deep pink and pale purplish pink bi-colored whereas flowers of plants of 'Forever Maxi Yellow' are yellow in color.

Plants of the new *Kalanchoe* can be compared to plants of the male parent, 'Taranak'. Plants of the new *Kalanchoe* differ from plants of 'Taranak' in the following characteristics:

1. Plants of the new *Kalanchoe* are larger and more vigorous than plants of 'Taranak'.
2. Flowers of plants of the new *Kalanchoe* are larger than flowers of plants of 'Taranak'.
3. Flowers of plants of the new *Kalanchoe* are deep pink and pale purplish pink bi-colored whereas flowers of plants of 'Taranak' are reddish pink and light pink bi-colored.

Plants of the new *Kalanchoe* can be compared to plants of the *Kalanchoe blossfeldiana* 'Wevano', not patented. In side-by-side comparisons, plants of the new *Kalanchoe* differ primarily from plants of 'Wevano' in the following characteristics:

1. Plants of the new *Kalanchoe* are larger and more vigorous than plants of 'Wevano'.
2. Plants of the new *Kalanchoe* are more freely branching than plants of 'Wevano'.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet (FIG. 1) is a side perspective view of a typical flowering plant of 'Dokalcasi' grown in a container.

Figure 2:
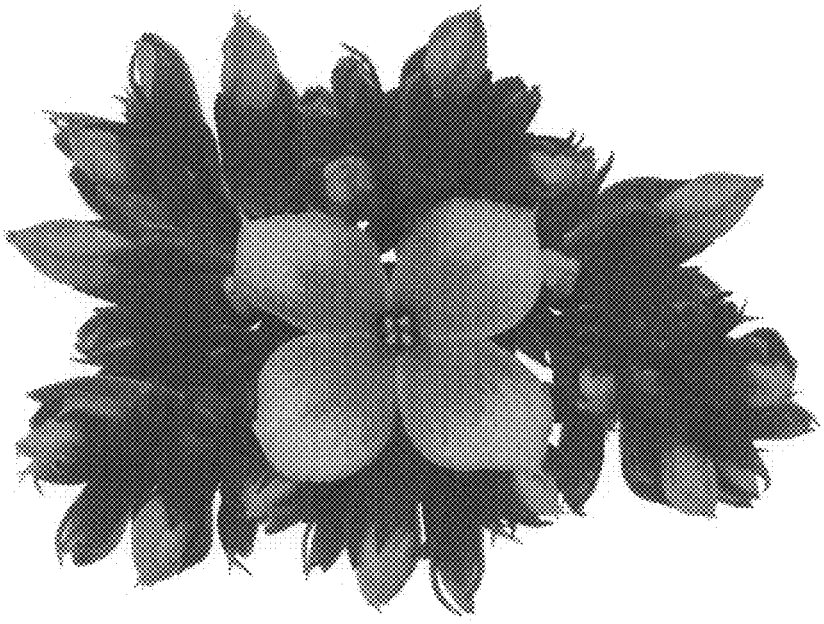

The photograph on the second sheet (FIG. 2) is a close-up view of a typical open flower and developing flower buds of 'Dokalcasi'.

DETAILED BOTANICAL DESCRIPTION

The aforementioned photographs and following observations, measurements and values describe plants grown during the spring and summer in 15.25-cm containers in a glass-covered greenhouse in De Lier, The Netherlands and under cultural practices typical of commercial *Kalanchoe* production. During the production of the plants, day temperatures ranged from 20° C. to 25° C., night temperatures ranged from 20° C. to 21° C. and light levels ranged from 10,000 lux to 55,000 lux. Plants received long day/short night conditions (more than 14 hours of light) for four weeks then plants received photoinductive short day/long night conditions (minimum 14 hours darkness) until flowering. Plants were 12 weeks old when the photographs were taken and 13 weeks old when the description was taken. In the detailed description, color references are made to The Royal Horticultural Society Colour Chart, 2007 Edition, except where general terms of ordinary dictionary significance are used.

Botanical classification: *Kalanchoe blossfeldiana* 'Dokalcasi'.

Parentage:

*Female, or seed, parent.*—*Kalanchoe blossfeldiana* 'Forever Maxi Yellow', not patented.

*Male or pollen parent.*—*Kalanchoe blossfeldiana* 'Taranak', not patented.

Propagation:

*Type.*—By vegetative terminal cuttings.

*Time to initiate roots, summer.*—About eleven days at temperatures about 21° C.

*Time to initiate roots, winter.*—About two weeks at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically greyish white to reddish brown in color, actual color of the roots is dependent on substrate composition, water quality, fertilizer type and formulation, substrate temperature and physiological age of roots.

*Rooting habit.*—Moderately freely branching; medium density to sparse.

Plant description:

*Plant and growth habit.*—Relatively large, upright and uniformly mounded plant habit; freely flowering habit with numerous cymes positioned above the foliar plane; triangular in shape with rounded crown; appropriate for 15.25-cm containers; vigorous growth habit and rapid growth rate.

*Plant height at flowering.*—About 32 cm.

*Plant diameter at flowering.*—About 28 cm.

*Branching habit.*—Freely branching habit with about 13 to 18 lateral branches developing per plant; pinching (removal of the terminal apex) is not required but will enhance lateral branch development.

Lateral branch description:

*Length.*—About 12 cm to 16 cm.

*Diameter.*—About 4 mm to 6 mm.

*Internode length.*—About 3 cm to 5 cm.

*Aspect.*—Mostly upright.

*Strength.*—Moderately strong to strong.

*Texture.*—Smooth, glabrous.

*Color, developing and developed.*—Close to 144B.

Leaf description:

*Arrangement.*—Opposite, simple; generally symmetrical.

*Quantity of leaves per lateral branch.*—At flowering, about 8 to 13 mature leaves and 12 to 18 generative leaves.

*Length.*—About 10.5 cm.

*Width.*—About 8.5 cm.

*Shape.*—Ovate to rounded.

*Apex.*—Obtuse.

*Base.*—Obtuse.

*Margin.*—Broadly crenate.

*Texture, upper and lower surfaces.*—Smooth, glabrous; coriaceous; succulent.

*Venation pattern.*—Pinnate.

*Color.*—Developing and fully developed leaves, upper surface: Close to 137A; venation, close to 137A to 137B. Developing and fully developed leaves, lower surface: Close to 137B; venation, close to 137B.

*Petioles*.—Length: About 1.2 cm. Diameter: About 4 mm to 7 mm. Strength: Moderately strong. Texture, upper and lower surfaces: Smooth, glabrous; coriaceous; succulent. Color, upper surface: Close to 137A. Color, lower surface: Close to 137B.

Flower description:

*Flower arrangement and habit*.—Single-type flowers arranged in axillary cymes; uniform and freely flowering habit with usually more than 25 open flowers and more than 25 flower buds per lateral branch and more than 200 open flowers and flower buds developing per plant; plants flower continuously for at least seven weeks; flowers face mostly upright to outwardly depending on the position in the inflorescence.

*Fragrance*.—None detected.

*Natural flowering season*.—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Early flowering habit, under short day/long night photoinductive conditions, plants begin flowering about eight to ten weeks; actual time to flower is primarily dependent upon temperature and light intensity.

*Post-production longevity*.—Excellent post-production longevity; plants maintain good foliage and flower substance for about 61 days under interior conditions; individual flowers last about 20 days on the plant; flowers persistent.

*Flower diameter*.—About 1.9 cm.

*Flower length* (*height*).—About 1.3 cm.

*Flower buds*.—Length: About 1 cm. Diameter: About 3 mm. Shape: Oblong, becoming tubular to ovoid with development. Texture: Smooth, glabrous. Color: Proximally, close to 138C and distally, close to 47D.

*Petals*.—Arrangement: Four in a single whorl. Length: About 9 mm. Width: About 6 mm. Aspect: Horizontal to slightly upright. Shape: Ovate. Apex: Mucronate to apiculate. Base: Obtuse. Margin: Entire. Texture and luster, upper and lower surfaces: Smooth, glabrous; glossy. Color: When opening, upper surface: Proximally, close to 52B and distally, close to 56C. When opening, lower surface: Proximally, close to 55C and distally, close to 56D. Fully opened, upper surface: Proximally, close to 52C and distally, close to 56C; venation, similar to lamina; proximal color becoming closer to 52D with development. Fully opened, lower surface: Proximally, close to 55D and distally, close to 56D venation, similar to lamina; color does not change with development.

*Sepals*.—Appearance: Four in a single whorl. Length: About 1 cm. Width: About 3 mm. Shape: Oblong, pointed. Apex: Acute. Base: Obtuse. Margin: Entire. Aspect: Upright, rigid. Texture and luster, upper and lower surfaces: Smooth; glabrous; glossy. Color, upper and lower surfaces: Close to 144A to 144B.

*Peduncles*.—Length: About 3 mm to 8 mm. Diameter: About 2 mm. Aspect: Erect, rigid. Strength: Strong. Texture: Smooth, glabrous. Color: Close to 138C.

*Reproductive organs*.—Androecium: Stamen number: About eight per flower. Filament color: Close to 150D. Anther length: About 0.3 mm. Anther shape: Elliptic, flat. Anther color: Close to 150D. Amount of pollen: Scarce. Pollen color: Close to 12A. Gynoecium: Pistil number: About four. Pistil length: About 1 cm. Style length: About 7 mm. Style color: Close to 138D. Stigma shape: Flat. Stigma color: Close to 8D, crystalline. Ovary color: Close to 138D.

*Seeds*.—Quantity per flower: If developed, up to 500 seeds per plant. Length: About 0.1 mm. Diameter: About 0.05 mm. Texture: Rough. Color: Close to 166C.

Temperature tolerance: Plants of the new *Kalanchoe* have been observed to tolerate temperatures from about 12° C. to about 35° C. and to be suitable for garden use.

Pathogen & pest tolerance: Plants of the new *Kalanchoe* have been observed to have moderate tolerance to Powdery Mildew (*Erysiphe cichoraceaum*). To date, plants of the new *Kalanchoe* have not been observed to be tolerant to pests and other pathogens common to *Kalanchoe* plants.

It is claimed:

1. A new and distinct *Kalanchoe* plant named 'Dokalcasi' as illustrated and described.

* * * * *